US012618061B2

(12) United States Patent
Mendonsa et al.

(10) Patent No.: US 12,618,061 B2
(45) Date of Patent: May 5, 2026

(54) METHODS OF GENE ASSEMBLY USING DNAZYMES AND USE IN DNA DATA STORAGE

(71) Applicant: Seagate Technology LLC, Fremont, CA (US)

(72) Inventors: Gemma Roselle Mendonsa, Edina, MN (US); Walter R. Eppler, Cranberry Township, PA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 384 days.

(21) Appl. No.: 17/816,215

(22) Filed: Jul. 29, 2022

(65) Prior Publication Data

US 2024/0035018 A1     Feb. 1, 2024

(51) Int. Cl.
| | |
|---|---|
| *C12N 15/113* | (2010.01) |
| *C12N 15/10* | (2006.01) |
| *G11C 11/54* | (2006.01) |
| *G11C 13/00* | (2006.01) |

(52) U.S. Cl.
CPC ........ *C12N 15/1031* (2013.01); *C12N 15/113* (2013.01); *G11C 13/0019* (2013.01); *C12N 2310/127* (2013.01); *C12N 2330/31* (2013.01); *G11C 11/54* (2013.01)

(58) Field of Classification Search
None
See application file for complete search history.

(56) References Cited

U.S. PATENT DOCUMENTS

| | | | |
|---|---|---|---|
| 10,370,246 B1 * | 8/2019 | Milenkovic | ............ G16B 30/10 |
| 10,417,457 B2 | 9/2019 | Peck | |
| 10,460,220 B2 | 10/2019 | Church | |
| 11,066,661 B2 | 7/2021 | Rausch et al. | |
| 2011/0099322 A1 | 4/2011 | Brownell et al. | |

FOREIGN PATENT DOCUMENTS

| | | | |
|---|---|---|---|
| WO | 2013178801 A2 | 12/2013 | |
| WO | WO-2019018410 A1 * | 1/2019 | ............ A61K 38/16 |

OTHER PUBLICATIONS

Yu et al. (Insight into an Oxidative DNA-Cleaving DNAZyme: Multiple Cofactors, the Catalytic Core Map and a Highly Efficient Variant, iScience, Oct. 23, 2020) (Year: 2020).*

(Continued)

*Primary Examiner* — Heather Calamita
*Assistant Examiner* — Elizabeth Rose Lafave
(74) *Attorney, Agent, or Firm* — Holzer Patel Drennan

(57) ABSTRACT

Building DNA strands at a high rate that are suitable for data storage. Methods include using DNAzyme and utilizing libraries of pre-prepared oligos. A system for the DNA strand synthesis includes: a DNA symbol library comprising a number of single strand oligo symbols; a DNA linker library comprising a first set of single strand oligo linkers and a second set of single strand oligo linkers; and a DNAzyme library comprising a number of DNAzymes. An S1 end of a first DNAzyme is adapted to join the S1 end of a symbol and an S2 end of the first DNAzyme is adapted to join an S2 end of a first linker, and an S1 end of a second DNAzyme is adapted to join an S1 end of a second linker and an S2 end of the second DNAzyme is adapted to join an S2 end of the symbol.

16 Claims, 10 Drawing Sheets

(56) References Cited

OTHER PUBLICATIONS

Gu et al. ("Portable, quantitative, and sequential monitoring of copper ions and pyrophosphate based on a DNAzyme-Fe3O4 nanosystem and glucometer readout," Analytical and Bioanalytical Chemistry, Jun. 2021) (Year: 2021).*

McManus et al. ("The Structural Diversity of Deoxyribozymes", Molecules, Sep. 6, 2010) (Year: 2010).*

Xiang et al. (Expanding DNAzyme Functionality through Enzyme Cascades with Applications in Single Nucleotide Repair and Tunable DNA-Directed Assembly of Nanomaterials, Chem. Sci. , published Jan. 1, 2013) (Year: 2013).*

Lindenburg et al. ("Split & mix assembly of DNA libraries for ultra-highthroughput on-bead screening of functional proteins", Nucleic Acids Res. , published Jun. 19, 2020) (Year: 2020).*

Ting et al. (Substrate specificity and kinetic framework of a DNAzyme with an expanded chemical repertoire: a putative RNaseA mimic that catalyzes RNA hydrolysis independent of a divalent metal cation, Nucleic Acids Research, 2004) (Year: 2004).*

* cited by examiner

METHODS OF GENE ASSEMBLY USING DNAZYMES AND USE IN DNA DATA STORAGE

BACKGROUND

There is always a desire for more data storage and increased speed writing to and reading from that storage, as well as a desire for reduced cost for the data storage.

DNA is an emerging technology for data storage. Current methods assert that a DNA strand or gene, to store 5 KB of data, can be written in 14 days. Comparatively, magnetic disk drives and magnetic tapes both can write 1 TByte in about an hour. A single DNA base pair location can store 2 bits; thus, 4000 Giga-base pairs would need to be stored in an hour to match the capabilities of a single disk drive or tape. Although current technology is believed to be capable of writing 15 base pairs an hour, there needs to be an 8 to 9 order of magnitude improvement in order for DNA data storage to be viable.

In addition to the speed differential between magnetic disk drives and tapes and DNA data storage, magnetic media data storage is a mature technology, optimized in many ways including cost. New processes need to be developed to make DNA data storage economical.

SUMMARY

This disclosure is directed to methods of building DNA strands, or genes, at a high rate that are suitable for data storage. The methods include using DNAzyme and utilizing libraries of pre-prepared oligos that are combined to form the desired DNA gene, encoding the desired data.

One particular implementation described herein is a system for making a DNA gene. One system comprises a DNA symbol library comprising a number of single strand oligo symbols, each symbol having an S1 end and an S2 end, a DNA linker library comprising a first set of single strand oligo linkers each having an S1 end and a second set of single strand oligo linkers each having an S2 end, and a DNAzyme library comprising a number of DNAzymes, each DNAzyme having an S1 end and an S2 end. The S1 end of a first DNAzyme is adapted to join the S1 end of a symbol and the S2 end of the first DNAzyme is adapted to join the S2 end of a first linker, and the S1 end of a second DNAzyme is adapted to join the S1 end of a second linker and the S2 end of the second DNAzyme is adapted to join the S2 end of the symbol.

Another particular system described herein comprises a first DNA symbol library comprising a number of single strand oligo first nibble symbols, each nibble symbol having a base section and an S1 end, a second DNA symbol library comprising a number of single strand oligo second nibble symbols, each nibble symbol having a base section and an S2 end, a DNA linker library comprising a first set of single strand oligo linkers each having an S1 end and a second set of single strand oligo linkers each having an S2 end, and a DNAzyme library comprising a number of DNAzymes, each DNAzyme having an S1 end and an S2 end. The base section of a first nibble symbol is adapted to join the base section of a second nibble symbol, the S1 end of a first DNAzyme is adapted to join the S1 end of the first nibble symbol and the S2 end of the first DNAzyme is adapted to join the S2 end of a first linker, and the S1 end of a second DNAzyme is adapted to join the S1 end of a second linker and the S2 end of the second DNAzyme is adapted to join the S2 end of the second nibble symbol.

Another particular implementation described herein is a method of making a DNA strand. The method comprises providing a DNA symbol library comprising a number of single strand DNA oligo symbols, each symbol having an S1 end and an S2 end, providing a DNA linker library comprising a first set of single strand DNA oligo linkers having an S1 end and a second set of single strand DNA oligo linkers having an S2 end, providing a DNAzyme comprising a number of DNAzymes having an S1 end and an S2 end, joining the S1 end of a first DNAzyme to the S1 end of a symbol and the S2 end of the first DNAzyme to the S2 end of a first linker, and joining the S1 end of a second DNAzyme to the S1 end of a second linker and the S2 end of the second DNAzyme to the S2 end of the symbol.

Other systems and methods are also described herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Figure 1:
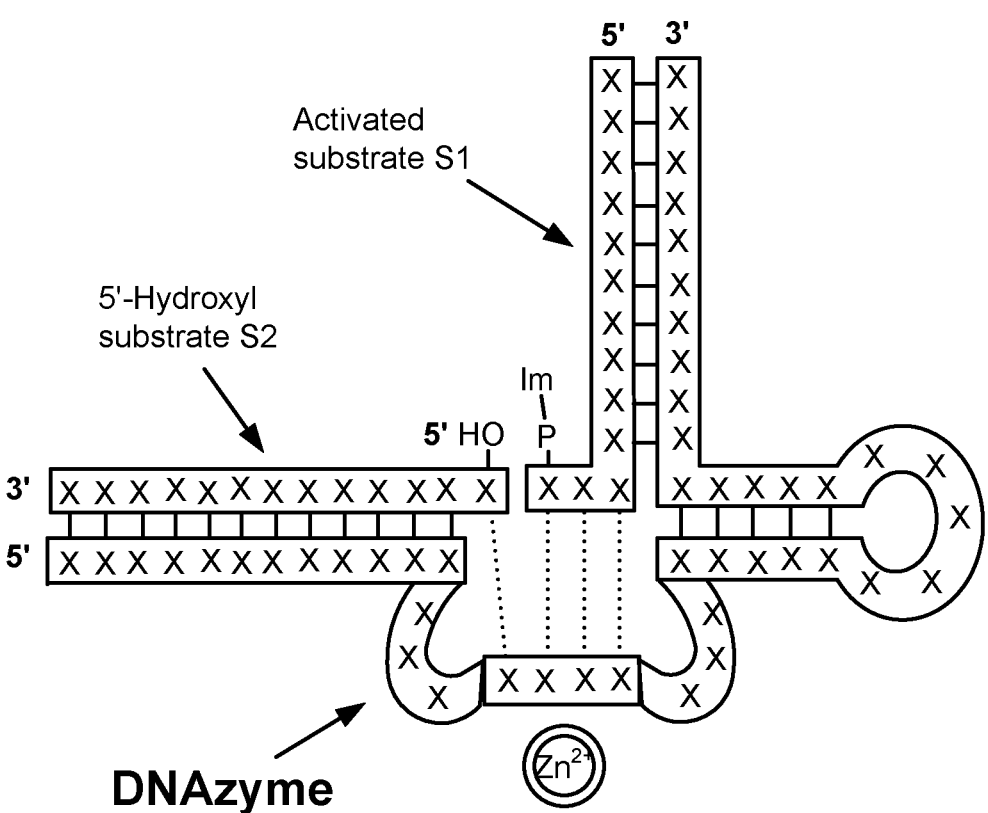
FIG. 1 is a schematic rendering of a DNAzyme joining two oligos.

As indicated above, various methods of building DNA strands or genes at a high rate are provided herein. The methods include utilizing libraries of pre-prepared oligos with DNAzyme to form the desired DNA structure or gene. For longer structures, mass parallelization can be used. If the gene is to be used as a data storage gene, the methods include assigning a bit pattern (e.g., 00, 01, 10, 11) to each nucleotide (A, C, G, T; where "A" refers to adenine, "C" refers to cytosine, "G" refers to guanine, and "T" refers to thymine), thus providing a gene encoding the desired data. It is noted that the methods described herein are directed to synthesizing a data storage gene, however the same methods are applicable to other applications that warrant DNA synthesis.

As indicated above, for a data storage gene, each nucleotide is assigned a bit pattern. In one example, A=00, C=10, G=01, and T=11. Multiple nucleotides form an oligo, and multiple oligos can be combined, by using DNAzyme, to eventually form a gene.

In accordance with the system described herein, multiple oligos are grouped in a library, with different nucleotide sequences being available in the library. An example of an oligo library is provided in Table 1, which lists pairs of nucleotides and a corresponding binary pattern.

TABLE 1

| DNA Oligo | Binary |
| --- | --- |
| AA | 0000 |
| AG | 0001 |
| AC | 0010 |
| AT | 0011 |
| GA | 0100 |
| GG | 0101 |
| GC | 0110 |
| GT | 0111 |
| CA | 1000 |
| CG | 1001 |
| CC | 1010 |
| CT | 1011 |
| TA | 1100 |
| TG | 1101 |
| TC | 1110 |
| TT | 1111 |

Using the example in Table 1 above, AA is 0000; the two base pair oligo stores 4 bits. As the oligo strand lengthens, more bits, bytes and data can be stored. For example, an oligo that is 8 base pairs long stores 16 bits, or 2 bytes. Using the example in Table 1, an oligo AATTAGTC is 0000111100011110, storing two bytes. It is noted that the example in Table 1 is an example of a primitive case and other bit mappings are possible where both the mapping and number of nucleotides per bit are different.

As indicated above, the system described herein utilizes libraries of oligos to synthesize DNA strands or genes using DNAzyme. The system includes a first library of oligos that are referred to herein as "symbols" and a second library of oligos that are referred to herein as "linkers." In general, when a symbol is used in synthesizing a data storage gene, the term "symbol" is used to represent an oligo that has a bit pattern. Additional details regarding symbols and linkers are provided below.

As seen from above, longer chain oligos (symbols and/or linkers) encode more data. Longer chains, however, typically require longer synthesis time. To decrease the time to synthesize longer chains, larger starting oligos can be used in the libraries.

For example, if the library has symbols that are 8 base pairs long, the system can store 16 bits per symbol. Having a DNA symbol library with larger symbols speeds up the synthesis time, but the number of symbols may not scale well. For symbols that are 8 base pairs long, the system would have 65,536 unique symbols in the library. For symbols that are 9 base pairs long, the system would have 262,144 unique symbols in the library. For symbols that are 10 base pairs long, the system would have 1,048,576 unique symbols. As shown in Table 2, the symbol library size is 4 to the power of the base pairs; i.e., the library size is $4^{(\text{base pairs per symbol})}$.

TABLE 2

| Base Pairs per Symbol | Number of Bits per Symbol | Size of Symbol Library |
| --- | --- | --- |
| 1 | 2 | 4 |
| 2 | 4 | 16 |
| 3 | 6 | 64 |
| 4 | 8 | 256 |
| 5 | 10 | 1024 |
| 6 | 12 | 4096 |
| 7 | 14 | 16,384 |
| 8 | 16 | 65,536 |
| 9 | 18 | 262,144 |
| 10 | 20 | 1,048,576 |

To form a DNA strand or gene of sufficient length to store usable amounts of data, multiple DNA symbols (i.e., at least two, often at least ten, more often at least twenty) from the library are combined using linkers and DNAzymes. Each symbol typically utilizes two linkers; one symbol may be combined with two linkers to form an intermediate strand, two intermediate strands are combined into a larger strand, etc. At least the first symbol and linkers are combined using DNAzyme. To control the connection of the symbols, linkers and DNAzyme to obtain the desired nucleotide sequence, the symbols, linkers and DNAzyme are provided with particular nucleotides at their ends.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

FIG. 1 illustrates an example DNAzyme, such as an E47 DNAzyme, as it ligates or joins two oligo strands, referred to herein as S1 and S2, where S1 is a 3'-phosphate-imidazole activated substrate and S2 is a 5'-hydroxyl substrate; this ligation occurs in the presence of zinc or copper ions, with zinc being shown in FIG. 1. It is noted that all of the S1 strand, the S2 strand and the DNAzyme are represented with generic nucleotides designated as "X"; it is understood that in actuality these X designations will be a nucleotide A, C, T, G. The DNAzyme catalyst molecule, e.g., E47, has a folded portion with a fixed sequence and structure; the 5' and 3' arms of the DNAzyme, however, tolerate modifications to the sequence. Any or all the DNAzyme, the 5' end of the S1 strand or the 3' end of the S2 strand can be modified to allow the S1 oligo to join to the DNAzyme and the S2 oligo to join to the DNAzyme. This ligation methodology is used to create stands that can be used for data encoding.

FIGS. 2A through 2E show examples of the components for forming a DNA strand or gene of sufficient length to store usable amounts of data according to this disclosure.

Figures 2A, 2B, 2C, 2D, 2E:
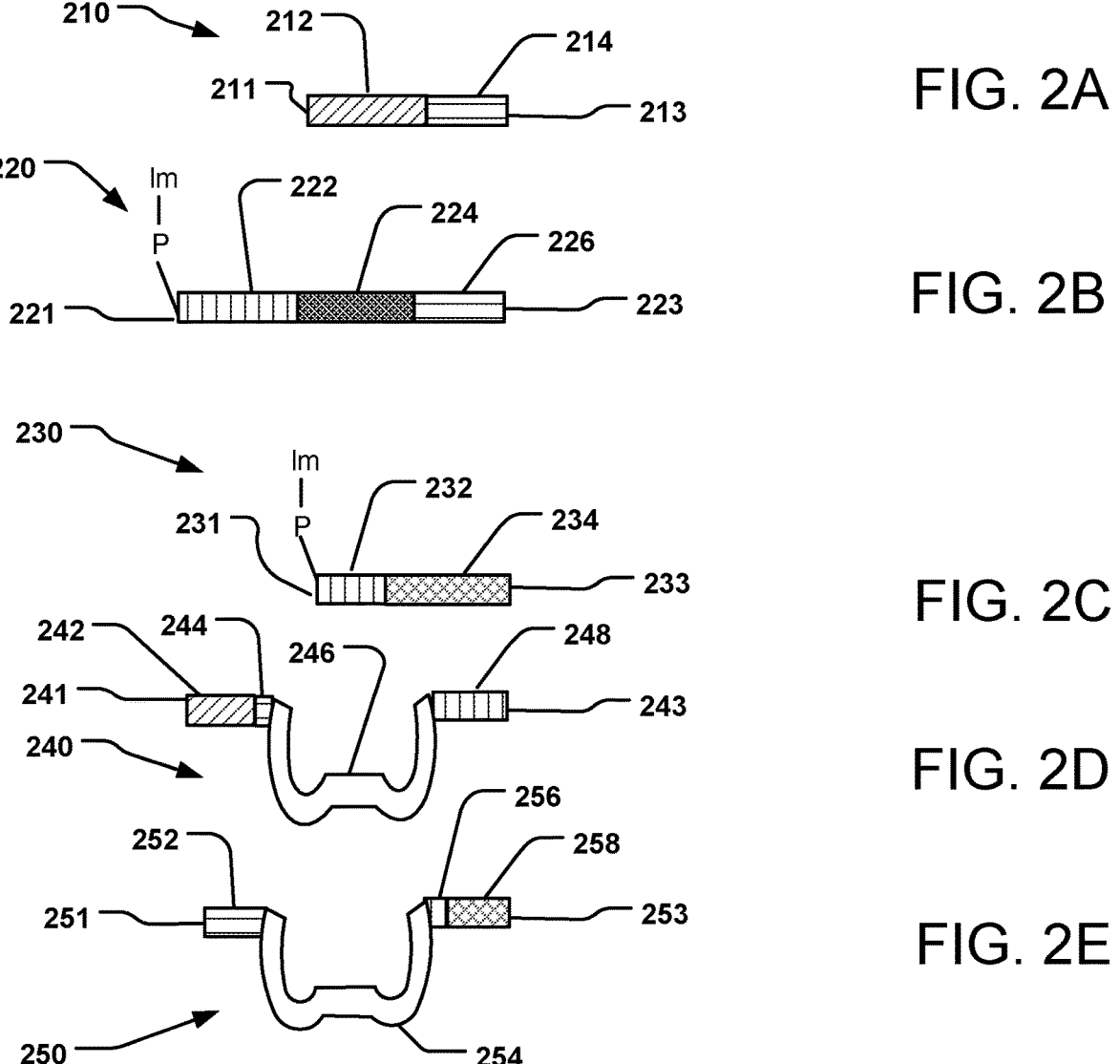
FIG. 2A is a schematic rendering of a first linker oligo.
FIG. 2B is a schematic rendering of a symbol oligo.
FIG. 2C is s schematic rendering of a second linker oligo.
FIG. 2D is a schematic rendering of a first DNAzyme.
FIG. 2E is a schematic rendering of a second DNAzyme.

In FIG. 2A a first oligo, referred to herein as a first linker 210, is shown. This linker 210 is a single strand, DNA fragment. This first linker 210 is shown with a first sequence section 212 at a first end 211 and a second sequence section 214 at a second end 213, each of the sections 212, 214 composed of a plurality of nucleotides.

FIG. 2B shows an oligo referred to herein as a symbol 220. This symbol 220 is a single strand, DNA fragment, typically longer than a linker (e.g., the linker 210). This symbol 220 is shown with a first sequence section 222 at a first end 221, a second (center) sequence section 224, and a third sequence section 226 at a second end 223, each of the sections 222, 224, 226 composed of a plurality of nucleotides. The first sequence section 222 at the first end 221 is an S1 end, and the third sequence section 226 at the second end is an S2 end. Additionally, the first sequence section 222 is shown with a phosphate-imidazole group, a conventional feature when using DNAzyme.

The symbol 220 will usually be composed of four to eight base nucleotides forming the section 224, with the S1 and S2 linking sections 222, 226 at each end. These S1 and S2 linking sections 222, 226 may have any number of nucleotides, e.g., less than the symbol base section 224, about the same, or more. In some embodiments, each of the linking sections 222, 226 will have about six to ten nucleotides.

FIG. 2C shows another oligo, referred to herein as a second linker 230. Similar to the first linker 210, the second linker 230 is a single strand, DNA fragment with a first sequence section 232 at a first end 231 and a second sequence section 234 at a second end 233, each of the sections 232, 234 composed of a plurality of nucleotides. The first sequence section 232 is shown with a phosphate-imidazole group, a conventional feature when using DNAzyme.

The linkers 210, 230 will usually be composed of six to 20 nucleotides, with the end nucleotides complimentary to either the ends of the symbol 220 or the DNAzyme ends, discussed below.

FIGS. 2D and 2E each show a DNAzyme, specifically, DNAzyme 240 (FIG. 2D) and DNAzyme 250 (FIG. 2E). The DNAzyme 240 has four sequence sections, a first sequence section 242 at a first end 241 of the DNAzyme 240, a second sequence section 244, a third sequence section 246, and a fourth sequence section 248 at the second end 243 of the DNAzyme 240, each of the sections 242, 244, 246, 248 composed of a plurality of nucleotides. The section 246 of the DNAzyme 240 is the E47 sequence whereas the sections 242, 244, 248 are tailored to the particular application. The sequence section 248 at the second end 243 is complimentary to an S1 end.

The DNAzyme 250 also has four sequence sections, a first sequence section 252 at a first end 251 of the DNAzyme 250, a second sequence section 254, a third sequence section 256, an a forth sequence section 258 at the second end 253 of the DNAzyme 250, each of the sections 252, 254, 256, 258 composed of a plurality of nucleotides. The section 254 of the DNAzyme 250 is the E47 sequence whereas the sections 252, 256, 258 are tailored to the particular application. The sequence section 252 at the first end 251 is complimentary to an S2 end.

Together, these linkers 210, 230, symbol 220 and DNAzymes 240, 250 are part of a system that can be used to form a DNA strand or gene. The linkers 210, 230 are part of a library of linkers; the symbol 220 is part of a library of symbols; and the DNAzymes 240, 250 are part of a library of DNAzymes. Each of the libraries is composed of multiple (e.g., hundreds, thousands, e.g, see Table 2) of oligos (linkers, symbols) and DNAzymes modified to ligate with the linkers and symbols.

Although the linkers 210, 230 are shown with two sections 212, 214 and 232, 234, respectively, it is to be understood that additional sections may be present in one or both linkers 210, 230. Additionally, the symbol 220 may have more (e.g., four or more) or less (e.g., two) sections. The DNAzymes 240, 250 have at least three sections, with one of the sections being the catalytic portion, e.g., E47.

Figure 3:
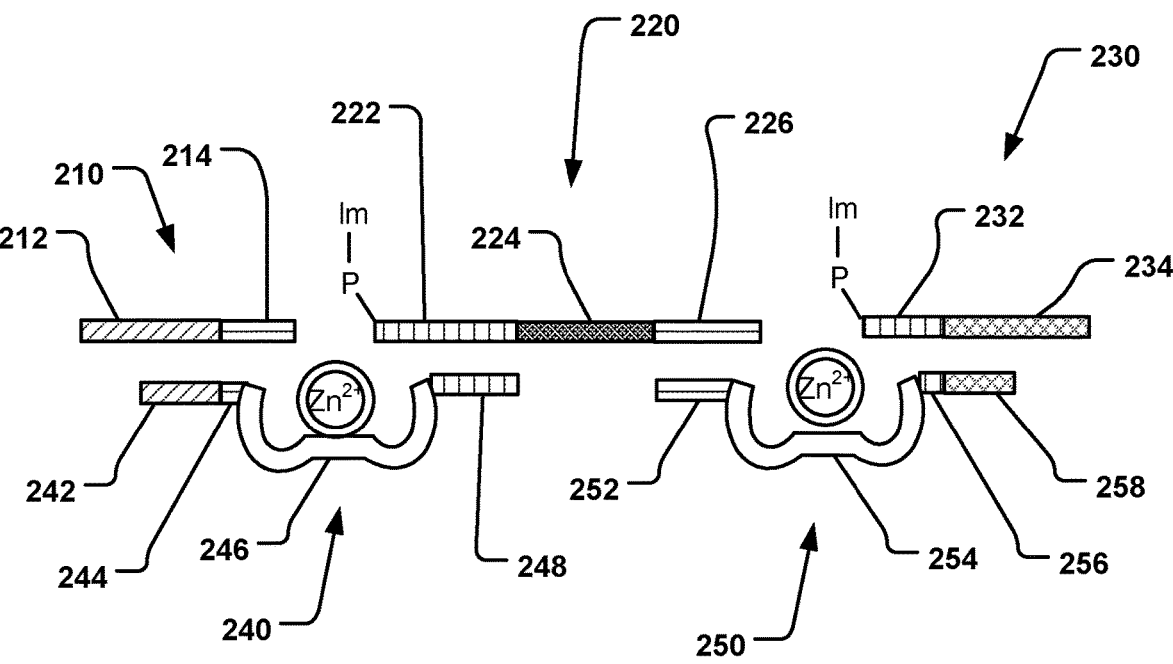
FIG. 3 is a schematic rendering of two DNAzymes linking a symbol oligo and two linker oligos.

The different patterns in the sequence sections designate different complementary sequences, those that will ligate, or join. FIG. 3 shows the oligos of FIGS. 2A through 2E ligated, in a particular order based on the sequence sections.

In FIG. 3, the first linker 210 is joined to the S2 first end 241 of the first DNAzyme 240; particularly, the sequence section 212 is complementary to and thus ligates with the sequence section 242 and the sequence section 214 is complementary to and ligates with the section 244. At the S1 second end 243 of the DNAzyme 240, the sequence section 248 is complementary to and ligates with the section 222 of the symbol 220 at the S1 first end 221. The second DNAzyme 250, particularly the sequence section 252 at the S2 first end 251, is complementary to and ligates with the S2 second end 223 of the symbol 220 at the section 226. At the second end 253 of the DNAzyme 250, the sequence section 256 is complementary to and ligates with the section 232 of the symbol 220 and the section 258 is complementary to and ligates with the section 234 of the symbol 230.

Figure 4:
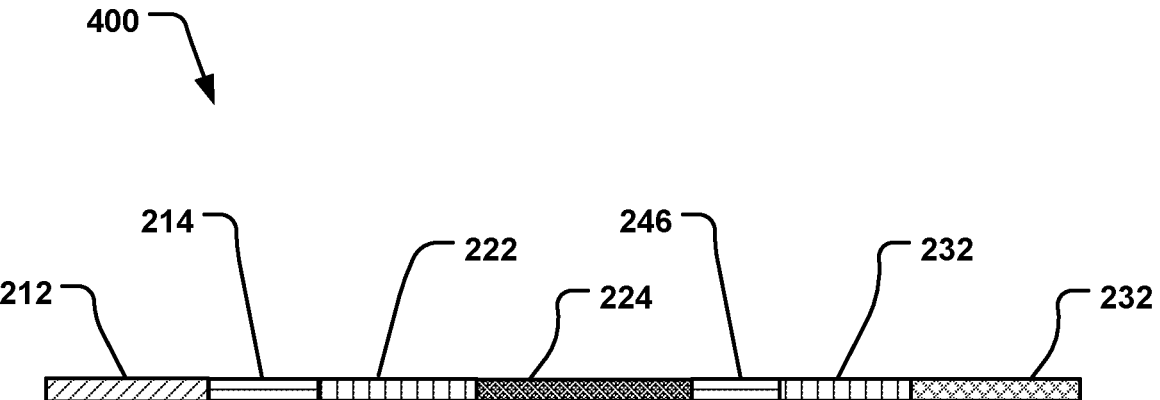
FIG. 4 is a schematic rendering of a DNA strand formed from the symbol oligo and two linker oligos of FIG. 3.

Summarized, the DNAzymes 240, 250 are used to attach the linkers 210, 230 to the symbol 220. In such a manner, a single strand DNA unit 400, shown in FIG. 4, is formed from the first linker 210, the symbol 220 and the second linker 230. As indicated above, the 3' end of the symbol 220 and the second linker 230, shown as the S1 first end 221 of the symbol 220 and the first end 231 of the linker 230, are 'activated' ends, activated by phosphate and imidazole before ligation. During ligation, the phosphate and imidazole release and do not appear in the final DNA unit 400. The DNAzymes 240, 250 are removed by various means, e.g., chemical or physical methods that can include heat, strand displacement, or conjugation to magnetic beads.

The DNA unit 400, as formed above, is faster and less expensive to form than DNA strands ligated using enzymes. By replacing enzymes with DNAzymes, the cost to form large DNA strands for data storage is greatly reduced. Using DNAzymes also increases the flexibility available during the assembly method. As shown above, DNAzymes can be used to attach linkers to symbols, eliminating the enzymes which can be the most expensive step, and additionally, DNAzymes can be used to assemble multiple DNA strands, e.g., unit 400, in downstream steps to form DNA strands or genes having sufficient length to encode usable amounts of data.

After the DNAzymes 240, 250 are used to attach the linkers 210, 230 to the symbol 220, an assembly method such as PCR (Polymerized Chain Reaction), an assembly method using Gibson Assembly® reagents, or another assembly method may be used to assemble the DNA strands (e.g., DNA unit 400), e.g., via complementary linkers. DNAzymes may also be used to join the DNA strands (e.g., DNA unit 400) together via their linkers in subsequent steps.

Figure 5:
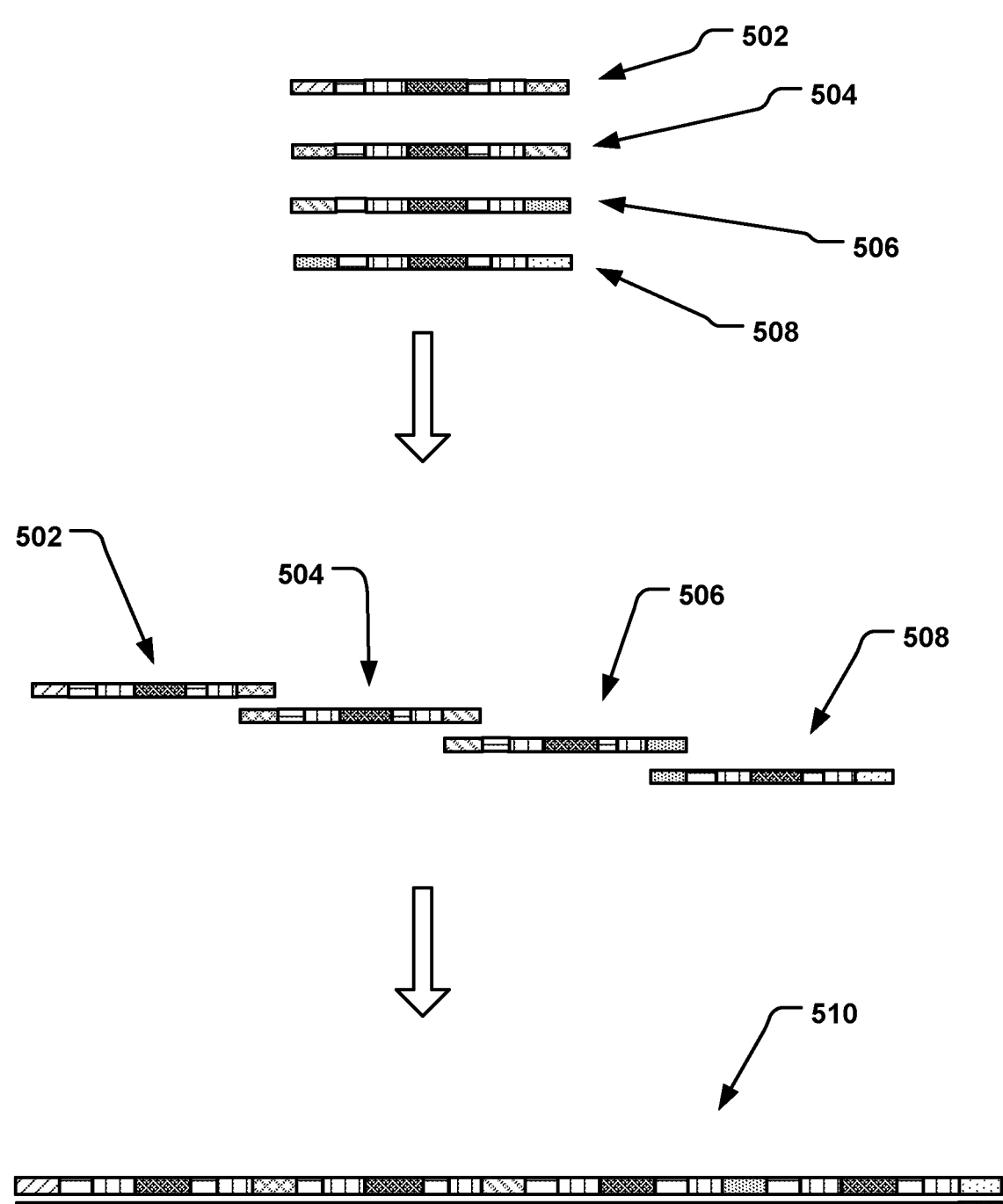
FIG. 5 is a schematic rendering of an example of steps for forming a DNA strand from a DNA strand of FIG. 4 via enzyme assembly.

FIG. 5 illustrates, step-wise, an example for assembly of multiple DNA strands (e.g., strands 400) into longer DNA strands.

In FIG. 5, four DNA strands 501, 502, 503, 504 are shown; each of these can have been prepared by the method described above using DNAzymes. The strands 501, 502, 503, 504 can be linked using an assembly PCR, an assembly method using Gibson Assembly® reagents, or other enzymatic assembly to form a longer strand 510, which is shown as a double strand, due to being formed by an enzyme assembly method.

Figure 6:
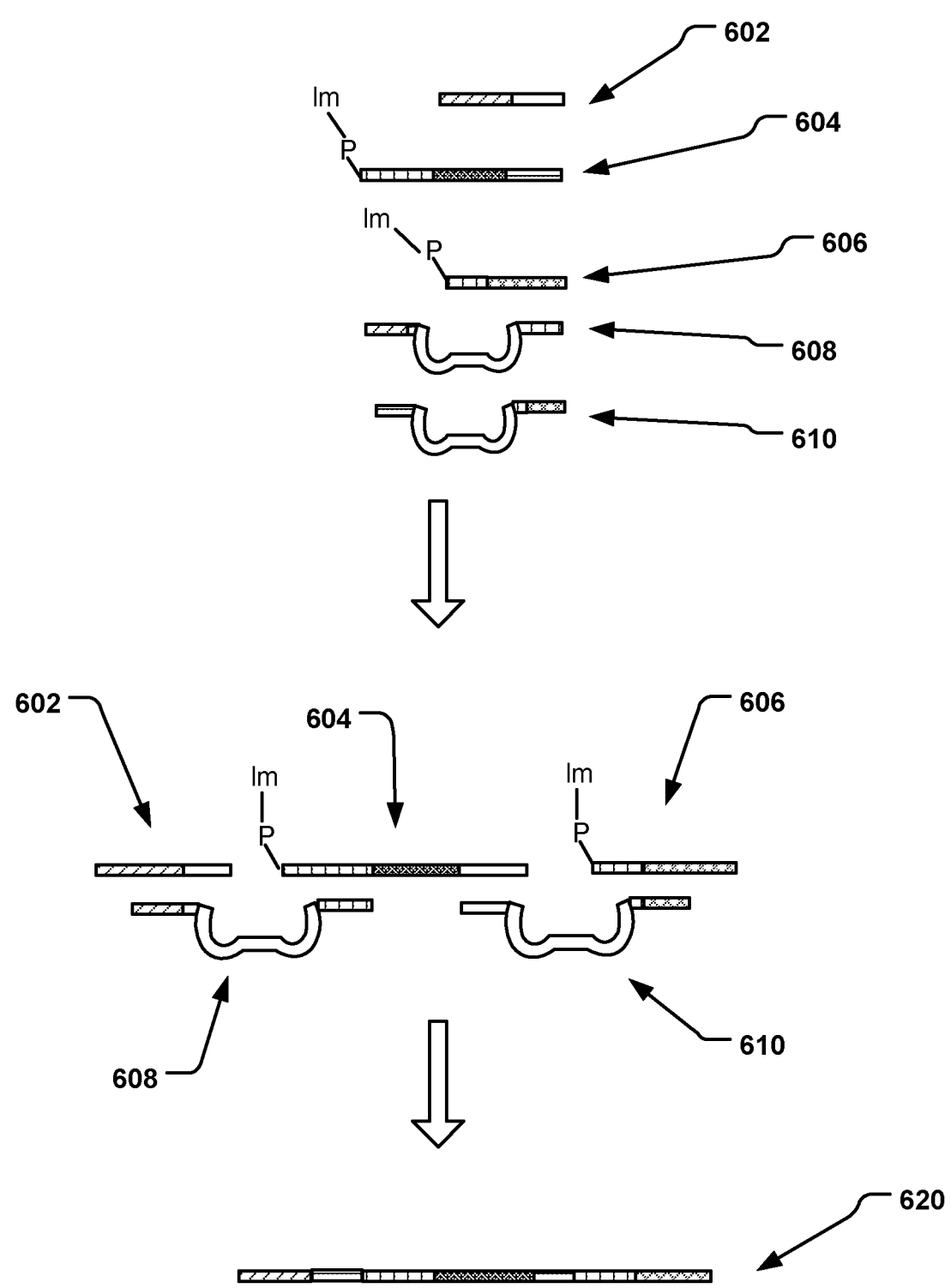
FIG. 6 is a schematic rendering of another example of steps for forming a DNA strand from a symbol oligo, two linker oligos, and DNAzymes.
Figure 7:
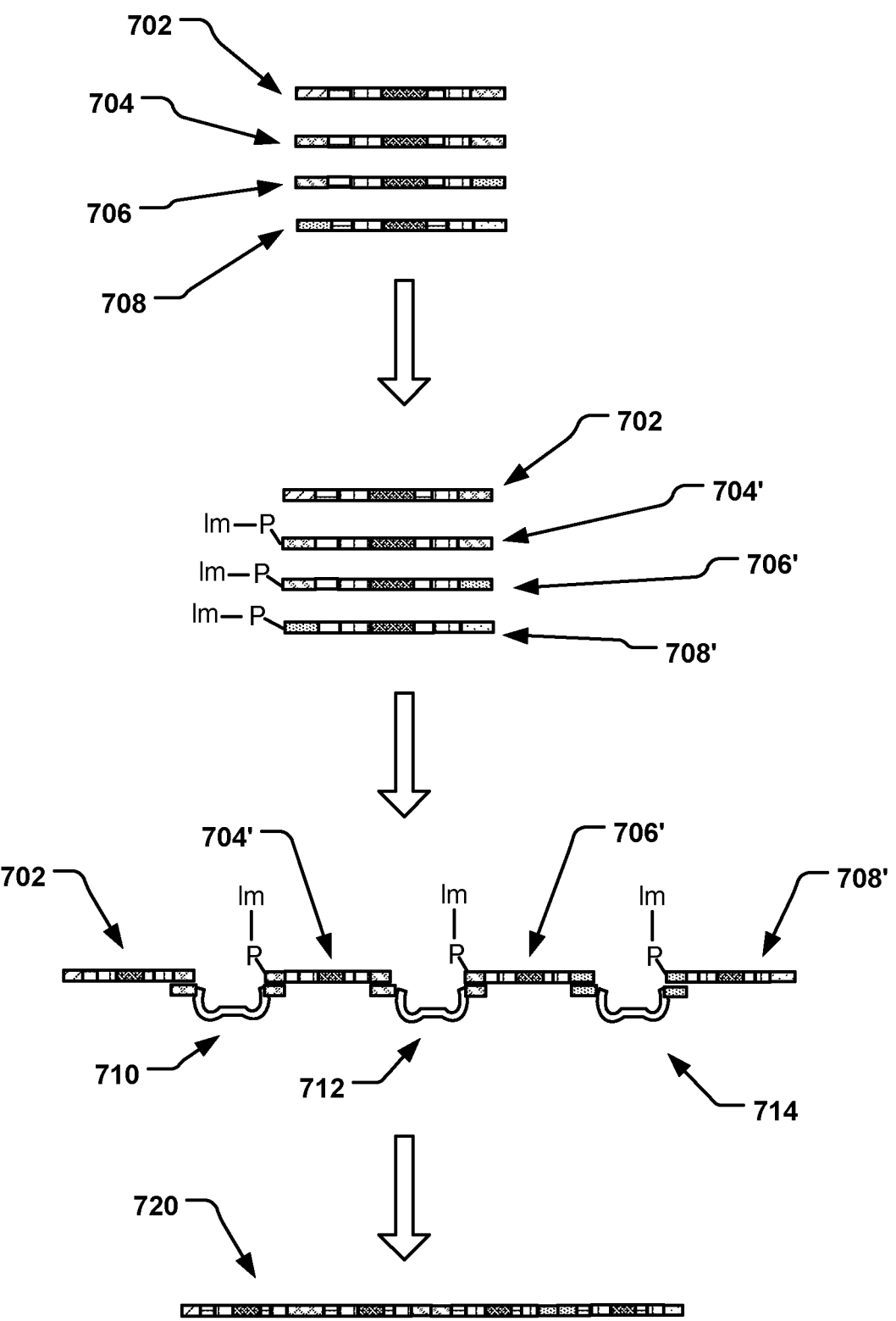
FIG. 7 is a schematic rendering of an example of steps for forming a DNA strand from DNA strands of FIG. 6 via DNAzyme assembly.

DNAzymes can be used at subsequent assembly steps, instead of just for attaching linkers to symbols. FIGS. 6 and 7 show another methodology for forming DNA strands sufficiently long for encoding data, this process using DNAzymes to join the previously-prepared DNA strands.

In FIG. 6, the process begins with a first linker 602 (e.g., from a linker library), a symbol 604 (e.g., from a symbol library) having an activated (phosphate-imidazole) end, a second linker 606 (e.g., from the same linker library or a separate linker library) having an activated (phosphate-imidazole) end, and a first DNAzyme 608 and a second DNAzyme 610.

The first linker 602 is joined to the symbol 604 via the first DNAzyme 608, as described above in respect to FIGS. 2A-2E, 3 and 4, and the second linker 606 is joined to the other end of the symbol 604 via the second DNAzyme 610. The result is a single strand DNA unit 620.

Four DNA strands 702, 704, 706, 708 are shown in FIG. 7; these strands correspond to the unit 620 of FIG. 6. FIG. 7 illustrates, step-wise, an example for assembly of multiple DNA strands (e.g., strands 702, 704, 706, 708) into longer DNA strands using DNAzymes.

At least three of the four strands 702, 704, 706, 708 have one end activated, e.g., with a phosphate-imidazole end; in this embodiment, the strands 704, 706, 708 are activated to form strands 704', 706', 708'.

The strand 702 is linked to the strand 704' via the DNAzyme 710, which is linked to the strand 706' via the DNAzyme 712, which is linked to the strand 708' via the DNAzyme 714, resulting in the single strand DNA strand 720.

Figure 8:
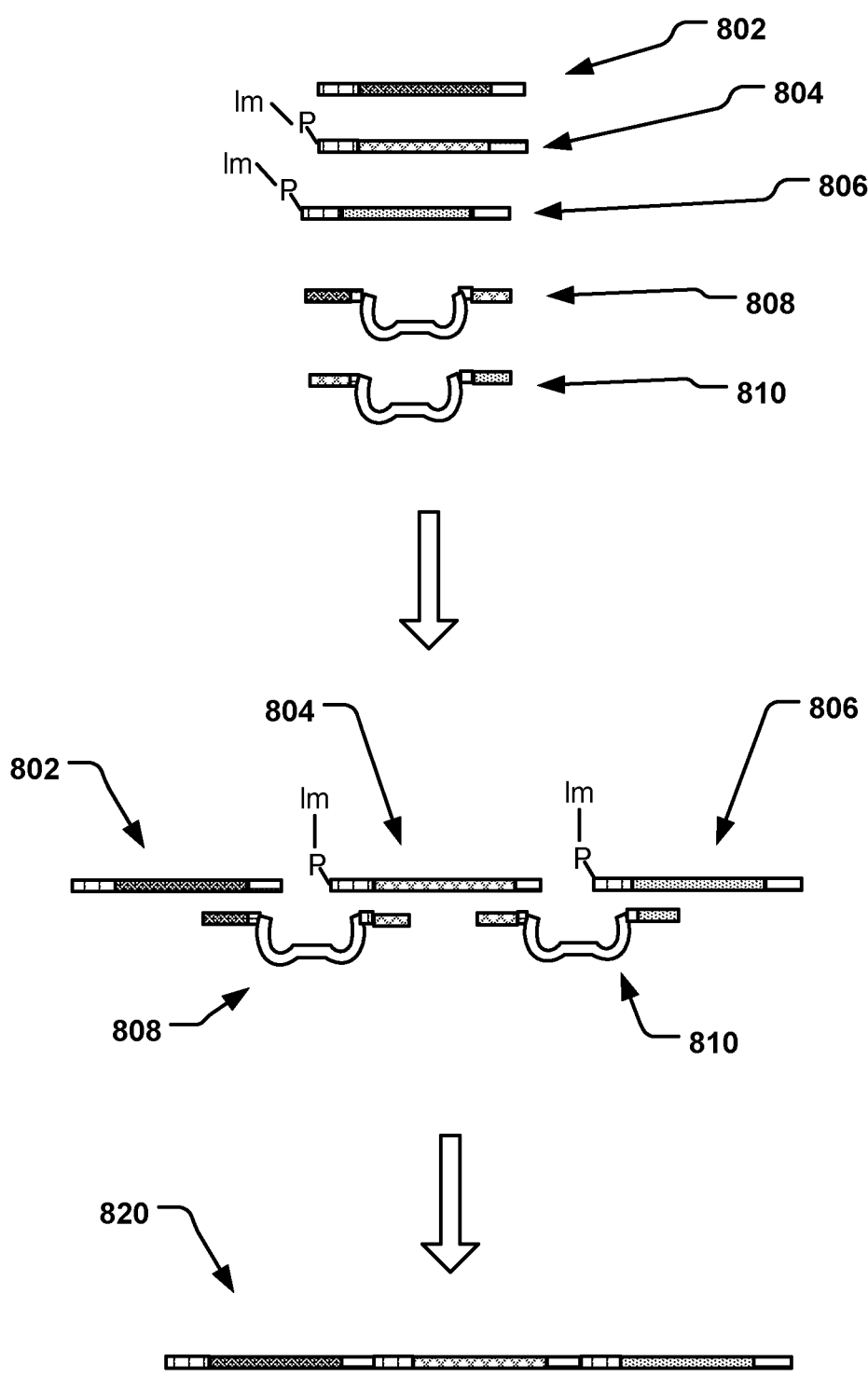
FIG. 8 is a schematic rendering of another example of steps for forming a DNA strand from a symbol oligo, two linker oligos, and DNAzymes.
Figure 9:
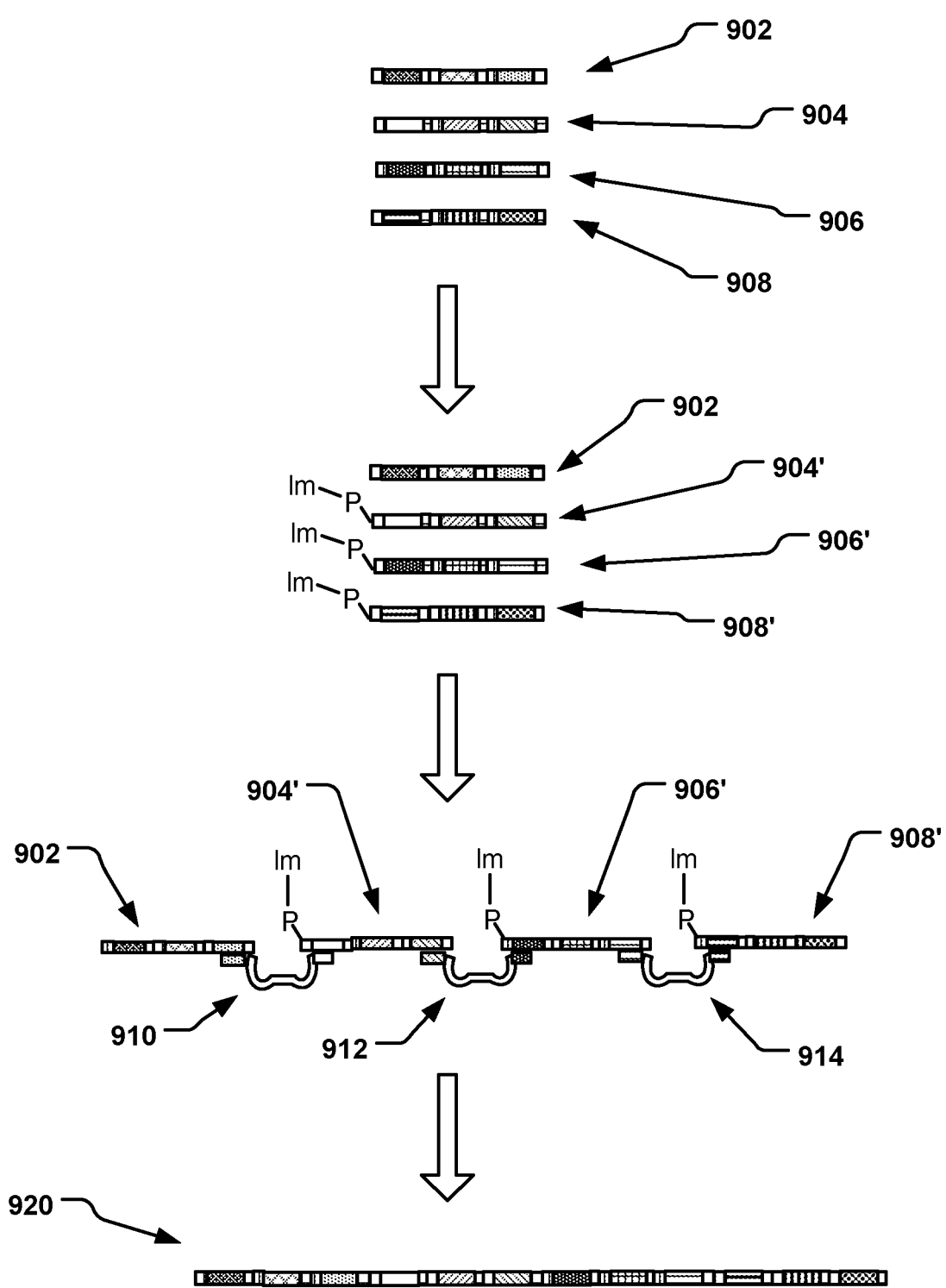
FIG. 9 is a schematic rendering of another example of steps for forming a DNA strand from DNA strands of FIG. 8 via DNAzyme assembly.

In another embodiment, symbols may be directly joined together by DNAzymes. FIGS. 8 and 9 show another methodology for forming DNA strands sufficiently long for encoding data, this process using symbols in place of linkers, thus eliminating the linker library.

In FIG. 8, the process begins with a first symbol 802 (e.g, from a symbol library), a symbol 804 (e.g., from the same symbol library or a separate symbol library) having an activated (phosphate-imidazole) end, another symbol 806 (e.g., from the same symbol library or a separate symbol library) having an activated (phosphate-imidazole) end, and a first DNAzyme 808 and a second DNAzyme 810.

The first symbol 802 is joined to the activated symbol 804 via the first DNAzyme 808 and the activated symbol 806 is joined to the other end of the symbol 804 via the second DNAzyme 810. The result is a single strand DNA unit 820.

Four DNA strands 902, 904, 906, 908 are shown in FIG. 9; these strands correspond to the unit 820 of FIG. 8. At least three of the four strands 902, 904, 906, 908 have one end activated, e.g., with a phosphate-imidazole end; in this embodiment, the strands 904, 906, 908 are activated to form strands 904', 906', 908'.

The strand 902 is linked to the strand 904' via the DNAzyme 910, which is linked to the strand 906' via the DNAzyme 912, which is linked to the strand 908' via the DNAzyme 914, resulting in the single strand DNA strand 920.

It is noted that in the method shown in FIGS. 8 and 9, where the symbols are directly joined together by DNAzymes, a larger DNAzyme library may be needed, in order to have ends corresponding to the various symbols.

In another embodiment, a symbol library can be split to create "nibble" libraries to reduce the overall symbol library size; e.g., one symbol library can be split into two, much smaller sub-libraries. For example, a 65,536 symbol library (see Table 2) can be reduced to a nibble library having 256 symbol nibbles. For example, each symbol oligo is split in half, where the two halves are called "nibbles" or "symbol nibbles." The first nibble has a base sub-section and a universal adaptor end and the DNAzyme has a complementary end that joins to the universal end. At its base end, the first nibble can join to any base end of any of the nibbles in the second nibble library. The nibbles in the second nibble library similarly have a base sub-section (that can join to any other nibble base) and a universal adaptor end that can join to a DNAzyme.

The nibbles are assembled to generate a symbol that has a short interrupting sequence in its middles. Linkers can then be attached to the nibble ends with DNAzymes. The unit now contains a symbol with two linkers attached, which can be assembled to other units, as in other embodiments.

Figure 10:
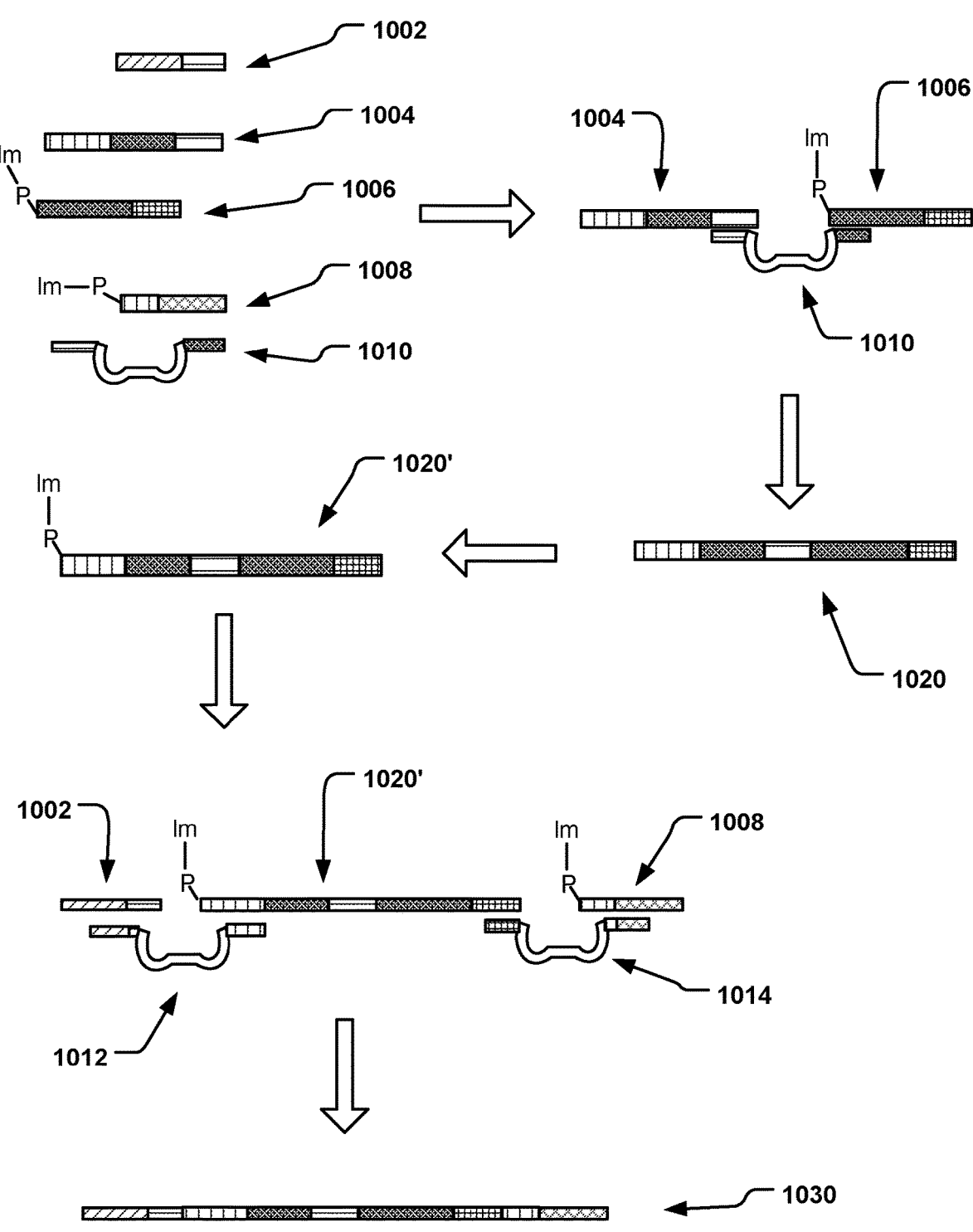
FIG. 10 is a schematic rendering of an example of steps for forming a DNA strand from two symbol nibbles, two linker oligos, and DNAzymes.

FIG. 10 shows another methodology for forming DNA strands sufficiently long for encoding data, this process using the shorter symbol nibbles. This process begins with a linker 1002 (e.g., from a linker library), a first symbol nibble 1004 (e.g., from a nibble library) having an activated (phosphate-imidazole) end, a second symbol nibble 1006 (e.g., from the same nibble library or a separate nibble library) having an activated (phosphate-imidazole) end, a second linker 1008 having an activated end, and a DNAzyme 1010.

The symbol nibble 1004 is joined to the symbol nibble 1006 via the DNAzyme 1010 and the result is a single strand DNA unit 1020. This unit or strand 1020 is activated, e.g., with a phosphate-imidazole end, to form strand 1020'.

The strand 1020' is joined to the linker 1002 via another DNAzyme 1010 and to the linker 1008 via another DNAzyme 1010; the result is a longer single strand 1030.

The previous discussion has provided example methods for forming DNA strands or genes using DNAzymes, starting with symbol oligos and linker oligos, the symbols and linkers each from a library. A strand formed with a DNAzyme can be further ligated using conventional enzyme assembly or additional DNAzymes.

By utilizing multiple symbols and multiple linkers, all of which are predetermined oligos, and utilizing parallel reactions, the synthesis rate of the final data storage gene is greatly improved compared to a de novo gene synthesis where each base pair is added one at a time.

In one particular implementation, the methods of this disclosure utilize a 16-bit symbol library having 65,536 unique DNA symbols (oligos), a linker library having 64 unique DNA linkers (oligos), and a DNAzyme library having 64 unique DNAzymes. Such as system can readily create a data storage gene that is 15 DNA symbols long, storing 30 bytes (140 bits) using about 600 base pairs. Each symbol is combined with corresponding linkers; multiple combinations can be done in parallel.

As one example, with the assumption that the symbols have eight base nucleotides in the base section and eight nucleotides in each end linking section, and the linkers have eight nucleotides, each symbol would need 40 base nucleotides. Thus, if a 15-symbol gene is made, it would have 600 base nucleotides.

The rate of synthesis of the gene depends on the number of nucleotide pairs in the symbols and the linkers. For example, if the linkers have three base nucleotides, the system can combine 63 symbols at one time to create a 126 byte data storage gene that requires two steps. If the linkers have five base nucleotides, the system can combine 1023 symbols at one time to create a 2048 byte data storage gene that requires two steps. Thus, the linker library provides a mechanism for readily combining the symbols in the desired order to form the data storage gene. It is noted that, generally, longer linkers (e.g., more than three base nucleotides, e.g., at least six base nucleotides) would be used to inhibit non-specific hybridization.

The DNA strand synthesis methods described above can be implemented in any manner, e g., utilizing various reactors, flasks, beakers, etc. The methods are also particularly suited to be done as a microfluidic lab-on-a-chip process.

Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as pico-liters) and are often called microfluidic systems. In digital microfluidics, the lab-on-a-chip has a hydrophobic "chip platform" on which fluid droplets (e.g., liquid droplets) can be manipulated by precisely controlled voltage application. The platform may have a cover plate covering the fluidic area. By utilizing the feature of surface tension of the fluid on the platform, the fluid can be precisely moved across the platform by voltage applied to the platform, e g., in a grid.

For the synthesis methods described above, the lab-on-a-chip is operably and fluidically connected to the symbol library, with each symbol retained in a well or other liquid storage compartment. Similarly, the lab-on-a-chip is operably and fluidically connected to the linker library, with each linker retained in a well or other storage compartment. In some designs, there may be at least 10,000 wells for the symbols, or at least 20,000, or at least 30,000 wells, or at least 65,000 wells. Additionally or alternately, there can be at least 10 wells for the linkers, or at least 15 wells, at least 30 wells, or at least 60 wells; there can be a similar number of wells for the DNAzyme, unless the DNAzyme is linking the symbols directly, as in FIG. 7, when additional wells will be warranted.

Using known techniques (e.g., voltage differential on the platform), the dispensed symbols and linkers are moved on (across) the platform and mixed in the desired steps. All mixing of the oligos (e.g., symbols and linkers) can be done on the platform or a dedicated mixing station may be used for one or more of the joining steps, e.g., utilizing heat and/or agitation. In some implementations, the platform may include a controllable reaction facilitator, such as a UV light source, and/or the final mixing station may include a voltage source, e.g., to align the completed gene to aid in collection.

One suitable (physical) size for a lab-on-a-chip is about 20 mm by 20 mm, which is compatible to an 8 inch wafer and could have 785,000 array elements, each array element having controllable voltage independently applied thereto. In some implementations, each well or other storage compartment for the oligos (symbols or linkers) or DNAzymes is 10× the size of an array element. This would provide 66,560 wells and leave 119,000 arrays for transport and mixing of the symbols and linkers on the platform.

The oligos (symbols or linkers) or DNAzymes may be provided to the wells and replenished as needed. Alternately, the symbols or linkers may be at least partially synthesized in or on the lab-on-a-chip. Instead of having a well or reservoir for each symbol and linker, different reagents (from off chip) can be used to synthesize the linkers and symbols, when needed, from individual nucleotides or from short groups of nucleotides, stored on-chip. This type of oligo synthesis can be done, e.g., via phosphoramidite synthesis or enzymatic synthesis.

A stacked or otherwise three-dimensional array of labs-on-a-chip would increase density and decrease required area for the synthesis. A drop elevator could be used to provide synthesis on multiple vertically stacked levels.

The above specification and examples provide a complete description of the structure and use of exemplary implementations of the invention. The above description provides specific implementations. It is noted that although not specifically stated, between any of the assembly steps described throughout this description, any additional steps may be added as needed or desired, for example, a PCR amplification step, a purification step, or both. Either of these steps could be performed after a Gibson an assembly step using Gibson Assembly® reagents. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A system for DNA synthesis, comprising:
a DNA symbol library comprising a number of single strand oligo symbols, each symbol having an activated 3'-phosphorimidazolide S1 end and a 5'-hydroxyl S2 end;
a DNA linker library comprising a first set of single strand oligo linkers each having a 3'-phosphorimidazolide S1 end and a 5'-hydroxyl S2 end, and a second set of single strand oligo linkers each having an activated 3'-phosphorimidazolide S1 end and a 5'-hydroxyl S2 end; and a DNAzyme library comprising a number of DNA ligating DNAzymes, each DNA ligating DNAzyme having a 3'-phosphorimidazolide complementary S1 end and a 5'-hydroxyl complementary S2 end;

wherein each of the linkers has a sequence specificity for the DNA ligating DNAzymes, and one or both of the S1 end and the S2 end of each of the linkers hybridizes to a complementary one of the DNA ligating DNAzymes; and wherein:

the S1 end of a first DNA ligating DNAzyme joins the S1 end of a symbol and the S2 end of the first DNA ligating DNAzyme joins the S2 end of a first linker, and the S1 end of a second DNA ligating DNAzyme joins the S1 end of a second linker and the S2 end of the second DNA ligating DNAzyme joins the S2 end of the symbol.

2. The system of claim 1, wherein the symbols comprise a base section having four to eight nucleotides, and a 3'-phosphorimidazolide S1 end section and a 5'-hydroxyl S2 end section each having six to ten nucleotides, independently.

3. The system of claim 2, wherein the symbols comprise two joined nibbles, each nibble having a base sub-section and an end section.

4. The system of claim 1, wherein the linkers comprise six to twenty nucleotides.

5. The system of claim 1, wherein the DNA ligating DNAzymes are E47 DNAzymes.

6. A system for DNA synthesis, comprising:

a first DNA symbol library comprising a number of single strand oligo first nibble symbols, each first nibble symbol having a base section and a 3'-phosphorimidazolide S1 end;

a second DNA symbol library comprising a number of single strand oligo second nibble symbols, each second nibble symbol having a base section and a 5'-hydroxyl S2 end;

a DNA linker library comprising a first set of single strand oligo linkers each having a 3'-phosphorimidazolide S1 end and a 5'-hydroxyl S2 end, and a second set of single strand oligo linkers each having a 3'-phosphorimidazolide S1 end and a 5'-hydroxyl S2 end; and a DNAzyme library comprising a number of DNA ligating DNAzymes, each DNA ligating DNAzyme having a 3'-phosphorimidazolide complementary S1 end and a 5'-hydroxyl complementary S2 end;

wherein:

wherein each of the linkers has a sequence specificity for the DNA ligating DNAzymes, and one or both of the S1 end and the S2 end of each of the linkers hybridizes to a complementary one of the DNA ligating DNAzymes;

the base section of a first nibble symbol joins the base section of a second nibble symbol;

the S1 end of a first DNA ligating DNAzyme joins the S1 end of one of the first nibble symbols and the S2 end of the first DNA ligating DNAzyme joins the S2 end of a first linker, and the S1 end of a second DNA ligating DNAzyme joins the S1 end of a second linker and the S2 end of the second DNA ligating DNAzyme joins the S2 end of one of the second nibble symbols.

7. The system of claim 6, wherein the first nibble symbols and the second nibble symbols have combined base sections having four to eight nucleotides, the first nibble symbol has a 3'-phosphorimidazolide S1 end section having six to ten nucleotides, and the second nibble symbol has a 5'-hydroxyl S2 end section each having six to ten nucleotides.

8. The system of claim 6, wherein the linkers comprise six to twenty nucleotides.

9. The system of claim 6, wherein, combined, the first DNA symbol library and the second DNA symbol library has 256 nibbles.

10. A method of making a DNA strand, comprising:

providing a DNA symbol library comprising a number of single strand DNA oligo symbols, each symbol having a 3'-phosphorimidazolide S1 end and a 5'-hydroxyl S2 end;

providing a DNA linker library comprising a first set of single strand DNA oligo linkers having a 3'-phosphorimidazolide S1 end and a second set of single strand DNA oligo linkers having a 5'-hydroxyl S2 end, wherein each of the linkers has a sequence specificity for the DNA ligating DNAzymes, and one or both of the S1 end and the S2 end of each of the linkers hybridizes to a complementary one of the DNA ligating DNAzymes;

providing a DNAzyme comprising a number of DNA ligating DNAzymes having a 3'-phosphorimidazolide complementary S1 end and a 5'-hydroxyl complementary S2 end;

joining the S1 end of a first DNA ligating DNAzyme to the S1 end of a symbol and the S2 end of the first DNA ligating DNAzyme to the S2 end of a first linker; and joining the S1 end of a second DNA ligating DNAzyme to the S1 end of a second linker and the S2 end of the second DNA ligating DNAzyme to the S2 end of the symbol.

11. The method of claim 10, wherein:

joining the S1 end of a first DNA ligating DNAzyme to the S1 end of a symbol and the S2 end of the first DNA ligating DNAzyme to the S2 end of a first linker; and joining the S1 end of a second DNA ligating DNAzyme to the S1 end of a second linker and the S2 end of the second DNA ligating DNAzyme to the S2 end of the symbol, are done simultaneously.

12. The method of claim 10, further comprising joining the DNA strand made in claim 10 with a second DNA strand.

13. The method of claim 12, wherein joining the DNA strand made in claim 10 with the second DNA strand is via an enzyme assembly.

14. The method of claim 12, wherein joining the DNA strand made in claim 10 with the second DNA strand is via another DNA ligating DNAzyme.

15. The method of claim 1, wherein the DNA ligating DNAzymes are E47 DNAzymes.

16. The system of claim 1, wherein the DNA ligating DNAzymes are E47 DNAzymes.

* * * * *